(12) United States Patent
Gajic et al.

(10) Patent No.: US 10,426,906 B2
(45) Date of Patent: Oct. 1, 2019

(54) VENTILATOR MONITORING AND CONTROL

(75) Inventors: Ognjen Gajic, Rochester, MN (US); Vitaly Herasevich, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 888 days.

(21) Appl. No.: 13/257,048

(22) PCT Filed: Mar. 18, 2010

(86) PCT No.: PCT/US2010/027838
§ 371 (c)(1),
(2), (4) Date: Sep. 16, 2011

(87) PCT Pub. No.: WO2010/108018
PCT Pub. Date: Sep. 23, 2010

(65) Prior Publication Data
US 2012/0000464 A1    Jan. 5, 2012

Related U.S. Application Data

(60) Provisional application No. 61/161,239, filed on Mar. 18, 2009.

(51) Int. Cl.
*A61M 16/00* (2006.01)
*A61B 5/00* (2006.01)
(Continued)

(52) U.S. Cl.
CPC ....... *A61M 16/0051* (2013.01); *A61B 5/0036* (2018.08); *A61B 5/03* (2013.01);
(Continued)

(58) Field of Classification Search
CPC .............. A61M 16/00; A61M 16/0051; A61M 2205/18; A61M 2205/33;
(Continued)

(56) References Cited

U.S. PATENT DOCUMENTS 3,973,240 A * 8/1976 Fong .............................. 375/212
5,603,315 A * 2/1997 Sasso, Jr. ................. 128/204.18
(Continued)

FOREIGN PATENT DOCUMENTS

JP    2002-336207    11/2002

OTHER PUBLICATIONS

Amato et al., "Effect of a protective-ventilation strategy on mortality in the acute respiratory distress syndrome," *N Engl J Med*, 338(6): 347-354, Feb. 1998.
(Continued)

*Primary Examiner* — Colin W Stuart
(74) *Attorney, Agent, or Firm* — Fish & Richardson P.C.

(57) ABSTRACT

A computer-implemented patient information provisioning method is disclosed. The method includes automatically extracting with a computer system, from records maintained for a patient under care in a healthcare facility, information from a electronic medical record; obtaining with the computer system information about a medical ventilator treating the patient; using the information from the electronic medical record and the information about the medical ventilator to determine whether a potentially dangerous condition exists with respect to the ventilator; and electronically alerting a caregiver if it is determined that a potentially dangerous condition exists.

25 Claims, 6 Drawing Sheets

(51) Int. Cl.
| | |
|---|---|
| A61B 5/03 | (2006.01) |
| A61B 5/08 | (2006.01) |
| A61B 5/091 | (2006.01) |
| A61B 5/087 | (2006.01) |
| A61B 5/085 | (2006.01) |

(52) U.S. Cl.
CPC .............. *A61B 5/036* (2013.01); *A61B 5/038* (2013.01); *A61B 5/08* (2013.01); *A61B 5/085* (2013.01); *A61B 5/087* (2013.01); *A61B 5/0816* (2013.01); *A61B 5/091* (2013.01); *A61M 16/00* (2013.01); *A61M 16/021* (2017.08); *A61B 5/412* (2013.01); *A61M 2205/18* (2013.01); *A61M 2205/33* (2013.01); *A61M 2205/3331* (2013.01); *A61M 2205/3344* (2013.01); *A61M 2205/3553* (2013.01); *A61M 2205/3569* (2013.01); *A61M 2205/3584* (2013.01); *A61M 2205/3592* (2013.01); *A61M 2230/205* (2013.01); *A61M 2230/40* (2013.01); *A61M 2230/435* (2013.01)

(58) Field of Classification Search
CPC .. A61M 2205/3303; A61M 2205/3306; A61M 2205/3331; A61M 2205/3344; A61M 2230/20; A61M 2230/202; A61M 2230/205; A61M 2230/40; A61M 2230/435; A61M 16/021; A61M 16/022; A61M 16/024; A61B 5/00; A61B 5/0036; A61B 5/03; A61B 5/036; A61B 5/038; A61B 5/0205; A61B 5/08; A61B 5/0816; A61B 5/082; A61B 5/083; A61B 5/087; A61B 5/091
USPC ............ 128/204.21, 200.24, 203.14, 204.18, 128/204.23, 204.22
See application file for complete search history.

(56) References Cited

U.S. PATENT DOCUMENTS

| | | | | |
|---|---|---|---|---|
| 5,694,926 | A * | 12/1997 | DeVries et al. | 128/205.24 |
| 5,832,450 | A * | 11/1998 | Myers | G06F 19/363 705/3 |
| 6,148,814 | A | 11/2000 | Clemmer et al. | |
| 2002/0013517 | A1* | 1/2002 | West et al. | 600/300 |
| 2002/0026941 | A1 | 3/2002 | Biondi et al. | |
| 2003/0010339 | A1* | 1/2003 | Banner | A61M 16/026 128/204.18 |
| 2005/0098178 | A1 | 5/2005 | Banner et al. | |
| 2005/0109340 | A1 | 5/2005 | Tehrani | |
| 2006/0047538 | A1* | 3/2006 | Condurso | G06F 19/326 705/3 |
| 2007/0000494 | A1* | 1/2007 | Banner et al. | 128/204.23 |
| 2007/0080801 | A1* | 4/2007 | Weismiller | A61B 5/411 340/539.13 |
| 2007/0129647 | A1* | 6/2007 | Lynn | A61B 5/00 600/538 |
| 2007/0244045 | A1* | 10/2007 | Holm et al. | 514/12 |
| 2007/0249951 | A1 | 10/2007 | Nieman et al. | |
| 2008/0072901 | A1 | 3/2008 | Habashi | |
| 2008/0281219 | A1 | 11/2008 | Glickman et al. | |
| 2008/0300572 | A1* | 12/2008 | Rankers | A61B 5/14532 604/504 |
| 2010/0082363 | A1* | 4/2010 | Warner | G16H 40/20 705/2 |

OTHER PUBLICATIONS

Bernard et al., "The American-European Consensus Conference on ARDS. Definitions, mechanisms, relevant outcomes, and clinical trial coordination," *Am J Respir Crit Care Med.*, 149(3 Pt 1):818-824, Mar. 1994.

Brun-Buisson et al., "Epidemiology and outcome of acute lung injury in European intensive care units. Results from the ALIVE study," *Intensive Care Med*, 30(1): 51-61, Jan. 2004.

Chambrin et al., "Multicentric study of monitoring alarms in the adult intensive care unit (ICU): a descriptive analysis," *Intensive Care Med*, 25(12): 1360-1366, Dec. 1999.

Chambrin, "Alarms in the intensive care unit: how can the number of false alarms be reduced?" *Crit Care* 5(4): 184-188, print Aug. 2001, Epub May 2001.

Dreyfuss et al., "High inflation pressure pulmonary edema. Respective effects of high airway pressure, high tidal volume, and positive end-expiratory pressure," *Am Rev Respir Dis*, 137(5): 1159-1164, May 1988.

Evans et al., "Computer surveillance of hospital-acquired infections and antibiotic use," *JAMA*, 256(8): 1007-1011, Aug. 1986.

Ferguson et al., "Acute respiratory distress syndrome: underrecognition by clinicians and diagnostic accuracy of three clinical definitions," *Crit Care Med*, 33(10): 2228-2234, Oct. 2005.

Gajic et al., "Risk Factors for Development of Acute Lung Injury (ALI)/ Acute Respiratory Distress Syndrome (ARDS) in Mechanically Ventilated Patients," *Proc Am Thorac Soc*, 2006, A832, 1 page.

Granton and Slutsky, "Venilator-induced lung injury," *Principles of Critical Care*, chapter 37, pp. 499-511, 2005.

Haug et al., "Decision support in medicine: examples from the HELP system," *Comput Biomed Res*, 27(5): 396-418, Oct. 1994.

Henderson et al., "Performance of computerized protocols for the management of arterial oxygenation in an intensive care unit," *Int J Clin Monit Comput* 8(4): 272-280, 1991.

Herasevich et al., "Electronic alert for detecting potentially injurious ventilator settings in patients with acute lung injury," *Crit Care Med.*, 36(12) (Suppl): A134, Abstract No. 533, 2 pages, Dec. 2008.

Herasevich et al., "Rule base system for identification of patients with specific critical care syndromes: The "sniffer" for acute lung injury," *AMIA Annu Symp Proc.*, p. 972, Oct. 2007.

Hickling et al., "Low mortality rate in adult respiratory distress syndrome using low-volume, pressure-limited ventilation with permissive hypercapnia: a prospective study," *Crit Care Med*, 22(10): 1568-1578, Oct. 1994.

Mandl et al., "Implementing syndromic surveillance: a practical guide informed by the early experience," *J Am Med Inform Assoc.*, 11(2): 141-150, Mar.-Apr. 2004.

McDonald, "Use of a computer to detect and respond to clinical events: its effect on clinician behavior," *Ann Intern Med* 84(2): 162-167, 1976.

McKinley et al, "Computerized decision support for mechanical ventilation of trauma induced ARDS: results of a randomized clinical trial," *J Trauma* 50(3): 415-424; discussion 425, Mar. 2001.

Miller, "Goal-directed critiquing by computer: ventilator management," *Comput Biomed Res.*, 18(5): 422-438, Oct. 1985.

Moorman et al., "Heart rate characteristics monitoring for neonatal sepsis," *IEEE Trans Biomed Eng*, 53(1): 126-132, Jan. 2006.

Moran et al., "Meta-analysis of controlled trials of ventilator therapy in acute lung injury and acute respiratory distress syndrome: an alternative perspective," *Intensive Care Med*, 31(2): 227-235, print Feb. 2005, Epub Jan. 2005.

Mullon et al, "Compliance with evidence-proven mechanical ventilation strategy in acute lung injury," *Proc Am Thorac Soc*, A570. 2006, 1 page.

Pittet et al., "Biological markers of acute lung injury: prognostic and pathogenetic significance," *Am J Respir Crit Care Med*, 155(4): 1187-1205, Apr. 1997.

Raschke et al, "A computer alert system to prevent injury from adverse drug events: development and evaluation in a community teaching hospital," *JAMA*, 280(15): 1317-1320, Oct. 1998.

Rivers et al., "Early goal-directed therapy in the treatment of severe sepsis and septic shock," *N Engl J Med* 345(19): 1368-1377, Nov. 2001.

Rubenfeld et al., "Incidence and outcomes of acute lung injury," *N Engl J Med*, 353(16): 1685-1693, Oct. 2005.

Schoenberg et al., "Making ICU alarms meaningful: a comparison of traditional vs. trend-based algorithms," *Proc AMIA Symp*, 379-383, 1999.

(56) References Cited

OTHER PUBLICATIONS

Shea et al., "Computer-generated informational messages directed to physicians: effect on length of hospital stay," *J Am Med Inform Assoc* 2(1): 58-64, Jan.-Feb. 1995.

Tehrani and Roum, "Intelligent decision support systems for mechanical ventilation," *Artif Intell Med*, 44(3): 171-182, print Nov. 2008, Epub Sep. 2008.

The Acute Respiratory Distress Syndrome Network, "Ventilation with lower tidal volumes as compared with traditional tidal volumes for acute lung injury and the acute respiratory distress syndrome," *N Engl J Med.*, 342(18):1301-1308, May 2000.

Umoh et al., "Patient and intensive care unit organizational factors associated with low tidal volume ventilation in acute lung injury," Crit Care Med 36(5): 1463-1468, May 2008.

Webb and Tierney, "Experimental pulmonary edema due to intermittent positive pressure ventilation with high inflation pressures. Protection by positive end-expiratory pressure," *Am Rev Respir Dis*, 110(5): 556-565, Nov. 1974.

International Preliminary Report on Patentability for PCT/US2010/027838, dated Sep. 20, 2011, 5 pages.

International Search Report and Written Opinion for PCT/US2010/027838, dated Oct. 29, 2010, 10 pages.

\* cited by examiner

VENTILATOR MONITORING AND CONTROL

CROSS-REFERENCE TO RELATED APPLICATIONS

This application is a National Stage application under 35 U.S.C. § 371 and claims benefit under 35 U.S.C. 119(a) of International Application No. PCT/US2010/027838, having an International Filing Date of Mar. 18, 2010, which claims priority to U.S. Provisional Patent Application Ser. No. 61/161,239, Ognjen Gajic et al., entitled "Ventilation Monitoring and Control," and filed Mar. 18, 2009, the contents of each are incorporated herein by reference.

TECHNICAL FIELD

This document relates to computer-based systems and techniques for monitoring a mechanical ventilator, such as a ventilator serving a patient in an intensive care unit or anywhere in a hospital, so that the ventilator does not harm the patient.

BACKGROUND

Critically ill patients in a hospital are often supported by a mechanical ventilator that assists them in their breathing. The ventilator provides pressurized air that is coordinated with a patient's natural breathing to help ensure that they obtain sufficient oxygen for normal metabolic activity.

Such support can be a cornerstone for treatment of problems such as acute lung injury (ALI), and in its more severe form, acute respiratory distress syndrome (ARDS). ALI is caused by problems such as sepsis, pneumonia, and other maladies. ALI is present, on average, in seven percent of ICU admissions and carries an in-hospital mortality rate of 40-50 percent. ALI is generally treated by keeping the PaO2>60 mmHg, without causing injury to the lungs with excessive O2 or volutrauma. Improperly-provided ventilation may result in ventilator-induced lung injury (VILI). Proper individualized settings for ventilator support may thus be important to prevent the ventilator itself from further damaging a patient's lung or lungs. However, caregivers frequently fail to recognize ALI/ARDS in patients who have it.

SUMMARY

This document describes systems and techniques that may be used to monitor the effect of a mechanical ventilator on a patient and to alert caregivers when the ventilation is potentially harmful to the patient. The systems and techniques may also be used to change ventilator settings to a more preferred setting. The monitoring may occur by using data feeds from various Electronic Medical Records sources in a hospital, including the hospital laboratory system (e.g., arterial blood gas analysis), natural language processing of diagnostic test reports (e.g., digital chest radiography), nursing observations (e.g., height and gender), and continuous monitoring at the ventilator itself (e.g., tidal volume, mode, and peak and plateau airway pressures). Such external data—i.e., data that is not generated by the ventilation system itself—may provide an indication that the patient is suffering from a lung injury, and that ventilation on the patient should occur at different levels than for a patient who does not have a lung injury.

In certain implementations, such systems and technique may provide one or more advantages. For example, patient care and safety may be improved when a system can monitor the patient automatically, and can do so using information that is not available from the ventilator itself. Also, where the system is connected to a communication system, a caregiver can be alerted and can address any dangerous situations that may arise. The alerts may be made judiciously, however, so that a caregiver will understand that the alerts are important when they are given. In addition, the alerts may be textual and contain information (e.g., including information about the patient's current condition), rather than simply being alarms, so that a caregiver can more readily understand the problem and quickly respond to it. Also, certain levels of follow-up may be provided, such as by recommending a change in treatment to a caregiver, or even making certain changes automatically where those changes have been determined to be helpful and safe. In this manner, patients having ALI and other problems may be protected from further damage to their lungs, and may receive superior care at a lower cost to the healthcare system.

In one implementation, a computer-implemented information presentation method is disclosed. The method comprises automatically extracting with a computer system, from records maintained for a patient under care in a healthcare facility, information from a electronic medical record; obtaining with the computer system information about a medical ventilator treating the patient; using the information from the electronic medical record and the information about the medical ventilator to determine whether a potentially dangerous condition exists with respect to the ventilator; and electronically alerting a caregiver if it is determined that a potentially dangerous condition exists. The information from the electronic medical record can comprise data from an arterial blood gas analysis. The method can also include obtaining with the computer system textual information from a medical report for the patient and using the textual information to determine whether a potentially dangerous condition exists with respect to the ventilator.

In some aspects, the information about the medical ventilator comprises information about a measured peak pressure or set tidal volume for the ventilator. Also, a potential dangerous condition can be determined to exist if the information from the electronic medical record indicates an arterial blood gas level of PaO2/FIO2<approximately 300, and the measured peak pressure is above about 35 mm H20 or the measured set tidal volume is above about 8 mL/kg predicted body weight (PBW). In addition, electronically alerting a caregiver can comprise providing an electronic messaging service with a description of an alerting condition of the patient, and information identifying the patient. Moreover, the method can include blocking alerting of the caregiver if the caregiver has previously been notified about the patient a predetermined number of times in a predetermined time period.

In another implementation, a computer system is disclosed that includes a medical ventilator for providing mechanical ventilation to a patient, one or more processors, memory, and one or more programs. The programs are stored in the memory and are configured to be executed by the one or more processors. They include instructions for automatically extracting, from records maintained for the patient, information from an electronic medical record; instructions for obtaining with the computer system information about the medical ventilator; instructions for using the information from the electronic medical record and the information about the medical ventilator to determine whether a potentially dangerous condition exists with respect to the ventilator; and instructions for electronically alerting a caregiver if it is determined that a potentially dangerous condition exists.

In yet another implementations, a computer-implemented patient information presentation system is disclosed. The system comprises one or more mechanical ventilators for treating patients in a healthcare facility; an interface operating on a computer processor system programmed to obtain data about operating parameters of the one or more ventilators and data from a central electronic medical records system operated by the healthcare facility; an electronic patient evaluator to use the data about the operating parameters of the one or more ventilators and the data from the central electronic medical records system to identify the presence of a potentially dangerous condition exists with respect to one or more ventilators; and an alert module to provide, for transmission to one or more caregivers, a notification of the identified dangerous condition.

In another implementation, a computer-implemented patient information presentation system is disclosed that comprises one or more mechanical ventilators for treating patients in a healthcare facility and an interface operating on a computer processor system programmed to obtain data about operating parameters of the one or more ventilators and data from a central electronic medical records system operated by the healthcare facility. The system also includes means for identifying presence of a potentially dangerous condition from the data about operating parameters and the data from a central electronic medical records system, and an alert module to provide, for transmission to one or more caregivers, a notification of the identified dangerous condition.

The details of one or more embodiments are set forth in the accompanying drawings and the description below. Other features and advantages will be apparent from the description and drawings, and from the claims.

DESCRIPTION OF DRAWINGS

Like reference symbols in the various drawings indicate like elements.

DETAILED DESCRIPTION

This document describes systems and techniques for identifying problematic operating conditions for a mechanical patient ventilator. The systems and techniques take into account data apart from the ventilator itself or currently-measured real-time patient data. Rather, the systems and techniques can combine ventilator data or real-time patient data, with historical patient data that is stored in an electronic medical record (EMR) system. In this manner, customizable "smart alarms" may be developed for notifying medical personnel when a potentially dangerous condition arises with a ventilator. Such alarms may take into account data such as laboratory results in an EMR (e.g., arterial blood gas analysis), natural language processing of diagnostic test reports (e.g., digital chest radiography), nursing observations (e.g., height and gender), and continuous monitoring at the ventilator itself (e.g., tidal volume, mode, and peak and plateau airway pressures).

In one example, when a patient who meets diagnostic criteria for ALI is ventilated with potentially injurious ventilator settings for one hour or longer, a respiratory therapist or other on-call caregiver receives a message, such as on a display pager or notification in an EMR, about the potential for injurious ventilation. The message may be suppressed if other warnings have previously been sent to the same caregiver about the same patient, in recent history, lest the caregiver not give full attention to the message.

Figure 1:
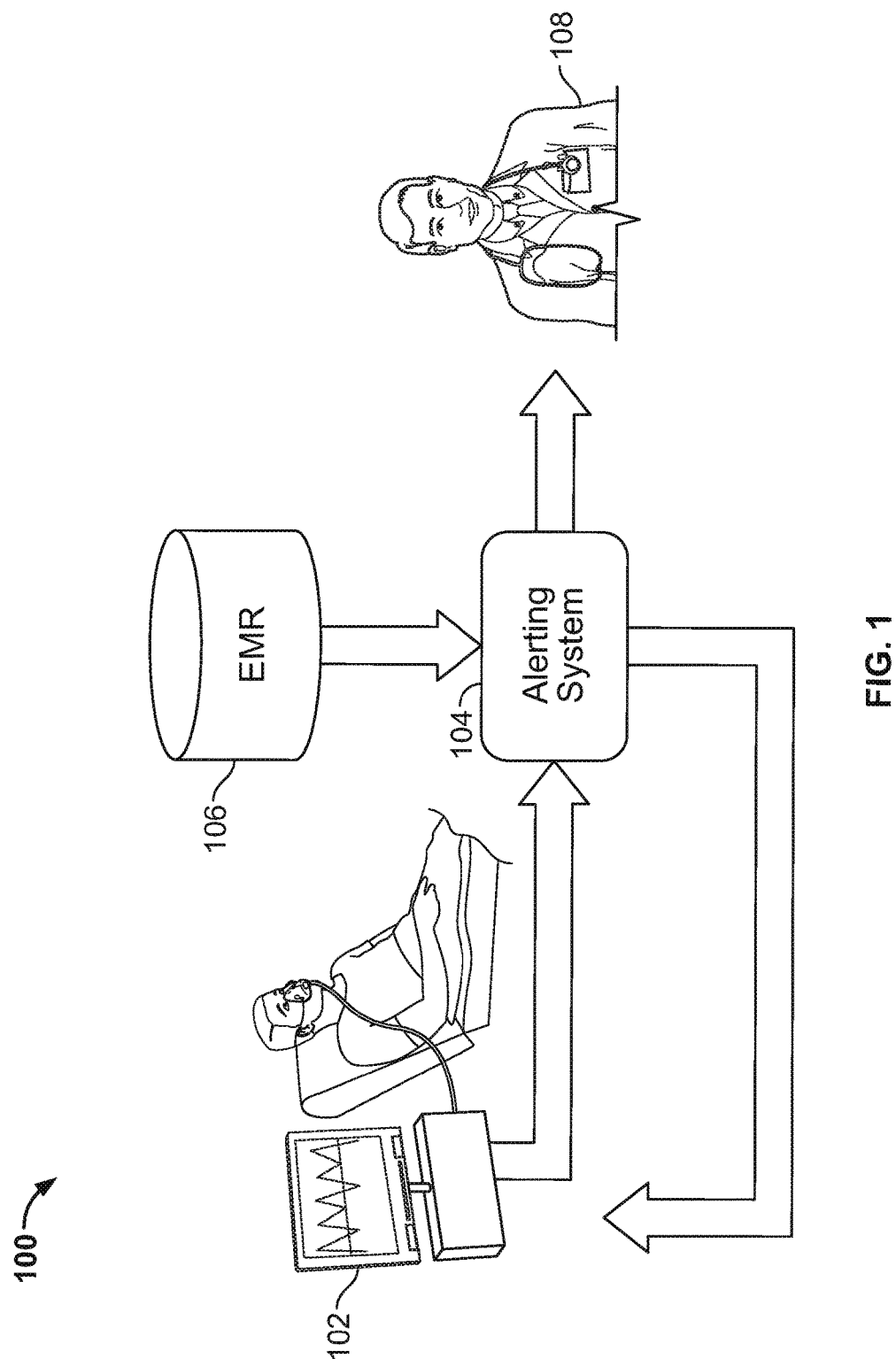
FIG. 1 is a conceptual flow diagram showing the processing of patient-related information into a clinical decision in aid of the patient.

FIG. 1 is a conceptual flow diagram showing the processing of patient-related information into a clinical decision in aid of the patient. In the figure, a patient information system 100 is shown as providing information about a patient to a caregiver 108. The patient is connected to a ventilator 102 and thus may be an ICU patient in relatively serious condition. The ventilator 102 includes electronic components for controlling the ventilator options and for identifying certain parameters associated with the ventilator 102, such as volume and pressure of air supplied to the patient by the ventilator 102.

Certain of such parameters may be read by an alerting system 104 that is in electrical or other such communication with the ventilator 102. The alerting system 104 may be a computer-implemented system that is programmed to gather patient-related information from multiple sources, including the controller for the ventilator 102, and to apply rules to such gathered data in order to determine whether a potentially dangerous situation exists for the patient. The alerting system 104 in this example also acquires information from an electronic medical record (EMR) system. Such gathering of information by the alerting system may occur periodically according to a clock associated with the alerting system 104, or it may occur in response to a patient-related event, such as a substantial change in ventilator parameter readings being provided to the alerting system 104 from the ventilator 102.

The information extracted by the alerting system 104 from the EMR system 106 can take a variety of forms. For example, laboratory results can be associated with certain conditions of the patient, and can be used to determine a user's response to the ventilator 102, and by extension, the condition of the patient with respect to ALI. Also, text in medical records can be identified and read by the system 100, and can be used to make matches to predetermined words.

The alerting system 104 is shown as sending communications to a caregiver 108. The communications may take a variety of familiar forms such as pager messages in text, or standard text messages, among other possibilities (e.g., data to be displayed in an app on a smart phone carried by the caregiver 108). The caregiver 108 may then read those messages, which, based on a determination made by the alerting system, will indicate that a dangerous condition may exist. The caregiver 108 may then return to the patient's room, review the ventilator and its parameters in more detail, and change those parameters to ensure the patient's safety. The caregiver 108 can also call into an ICU and direct another caregiver to modify a course of treatment for the patient.

Also, modification of the ventilator's operation can be achieved automatically rather than manually, and is shown in the figure by an arrow leading back from the alerting system 104 to the ventilator 102. For example, the alerting system may determine that the ventilator 102 setpoint for a particular parameter is at a potentially unsafe level, and may provide a new setpoint that the ventilator 102 may subsequently follow, at least until caregiver 108 can turn their attention to the ventilator 102 and manually override whatever setpoint has been automatically selected. Limitations may also be provided so that only setpoints previously determined to be safe under all conditions will be selected by the alerting system 104.

Figure 2A:
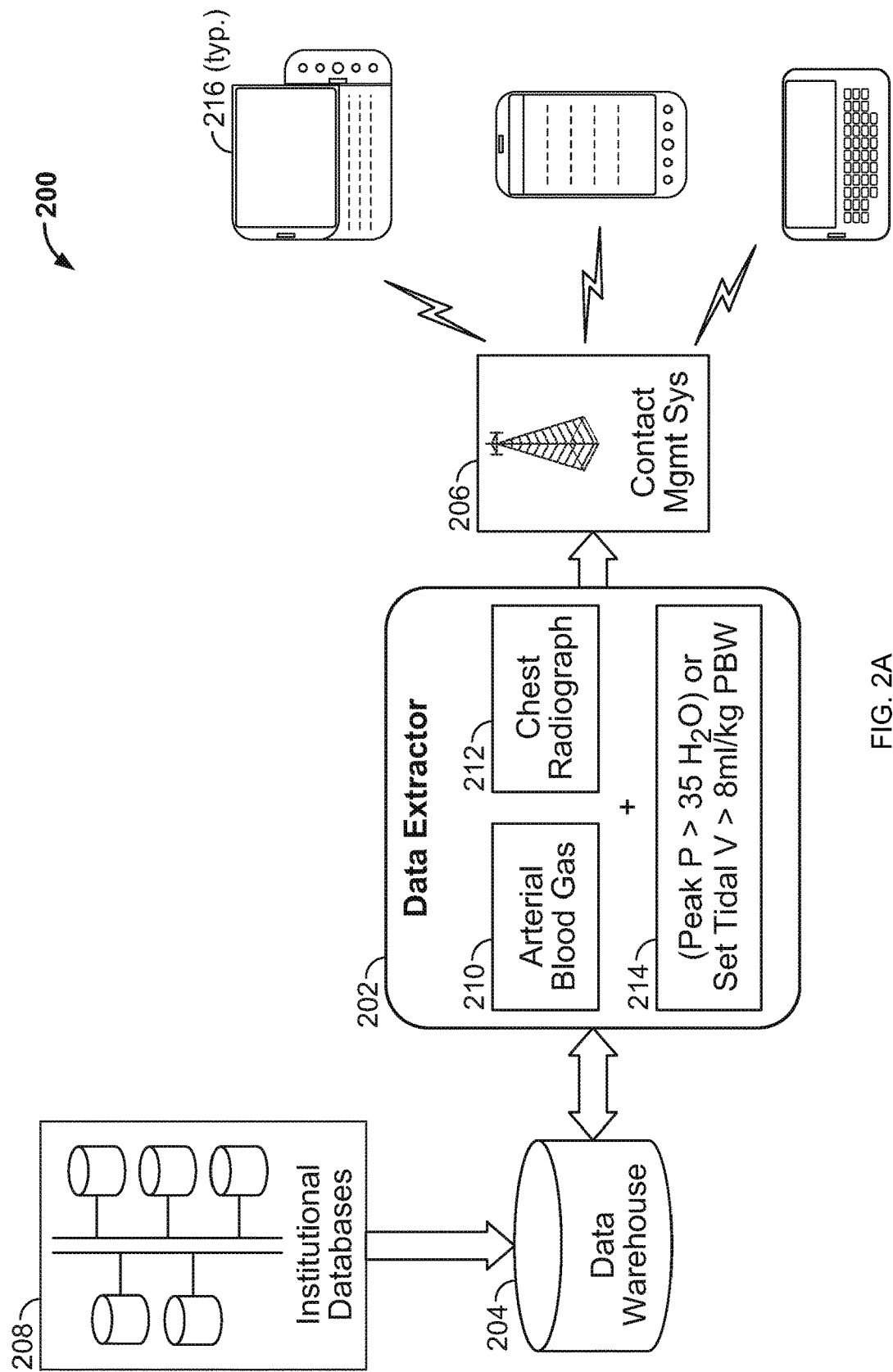
FIG. 2A is a block diagram showing processing of various patient-related data in order to generate an alert for a caregiver.

FIG. 2A is a block diagram showing processing of various patient-related data in order to generate an alert for a caregiver. Such processing occurs by use of an alerting system 200. The alerting system 200 may include a data extractor 202 and contact management system 206 that are added to an existing electronic medical record system so as to provide alerting functionality. The existing system may include a variety of institutional databases 208 that may take a variety of forms, and may be used by a healthcare institution in its ordinary course of business. Such databases could range from EMR databases of various types, to accounting databases and databases used to assist caregivers with making diagnoses. The existing system may also include a data warehouse 204, which may be provided with read access to various portions of the institutional databases 208 and may be employed to extract information from the institutional databases 208 and reformat and store the data where it can be queried and otherwise manipulated more readily.

The data extractor 202 may then be triggered by an internal clock on a periodic basis to extract data from the data warehouse 204, where the relevant data, in this example, relates to conditions of patients in a healthcare system who are currently on ventilators. Two particular pieces of data are gathered in this instance. First, information from a laboratory report on the patient's arterial blood gas level may be retrieved and identified. In particular, blood gas levels of PaO2/FiO2 below a certain level, such as about 300, may indicate that the patient suffers from ALI (box 210). Second, information from a patient's chest radiograph report may be obtained from the patient's medical records (box 212). Textual annotations in the report may be extracted, either by simple parsing from an electronic record or by OCR, and a search may be made for certain trigger terms such as ("bilateral" and "infiltrate") or "edema"— terms that indicate that the patient may have lung damage indicative of ALI.

The data extractor 202 may also at this point identify real-time or near real-time data form the patient's ventilator that indicates the current setting for the ventilator in terms of pressure and/or volume (box 214). The data extractor 202 may then apply one or more rules to the extracted data to make a determination about whether a dangerous condition is likely to exist for the patient. In this example, the determination is made if the arterial blood gas data shows PaO2/FiO2<300 (or less than about 300), the chest radiograph mentions the terms quoted above, and the peak pressure on the ventilator is over 35 mm of H₂O or the set tidal volume is greater than 8 mL/kg PBW (predicted body weight) or a similar amount to also indicate a problematic and potentially dangerous ventilator setting.

If the data extractor 202 makes a determination that a potentially dangerous condition exists, it may send a signal to a contact management system 206, which may be a system that prepares and routes a variety of messages to mobile devices 216 of caregivers in the system 200. Such preparation and routing, in this example, may include an initial determination by the system 200 of the caregiver that is currently responsible for respiration of the patient, such as an on-call respiratory therapist assigned to an ICU where the patient is stationed. The preparation may further include the generation of a message whose text indicates an identity of the patient, either directly (by name) or indirectly (by location in the ICU) and the nature of the condition that triggered the notification.

In certain circumstances, the generation of an alerting message may be blocked or delayed. Typically, such action may occur to prevent the generation of false positive reports that would result in caregivers having less respect for the system 200, and in the quality of care for patients declining. For example, the system 200 may require that an alerting condition be present for a certain number of cycles of the system 200, such as over a period of several hours. Also, the system 200 may limit the number of notifications that a particular caregiver receives, so that the caregiver is not being bombarded with notifications about a particular patient, and is rendered unable to determine which are serious and which are not.

In this manner, the system 200 can automatically identify potential dangerous conditions for a patient on a ventilator even if no caregiver has yet to make a determination that the patient has ALI or is likely to have ALI. The system 200 can also generate an alert that is custom, in that it can be transmitted remotely to a caregiver using whatever messaging technology the caregiver prefers (e.g., smart phone, text pager, etc.) and can give information about the nature of the alert. In addition, it can manage the number and type of message that is delivered so that the overall operation of system 200 is not overly intrusive to caregivers. As a result, the care of a patient may be improved.

Figure 2B:
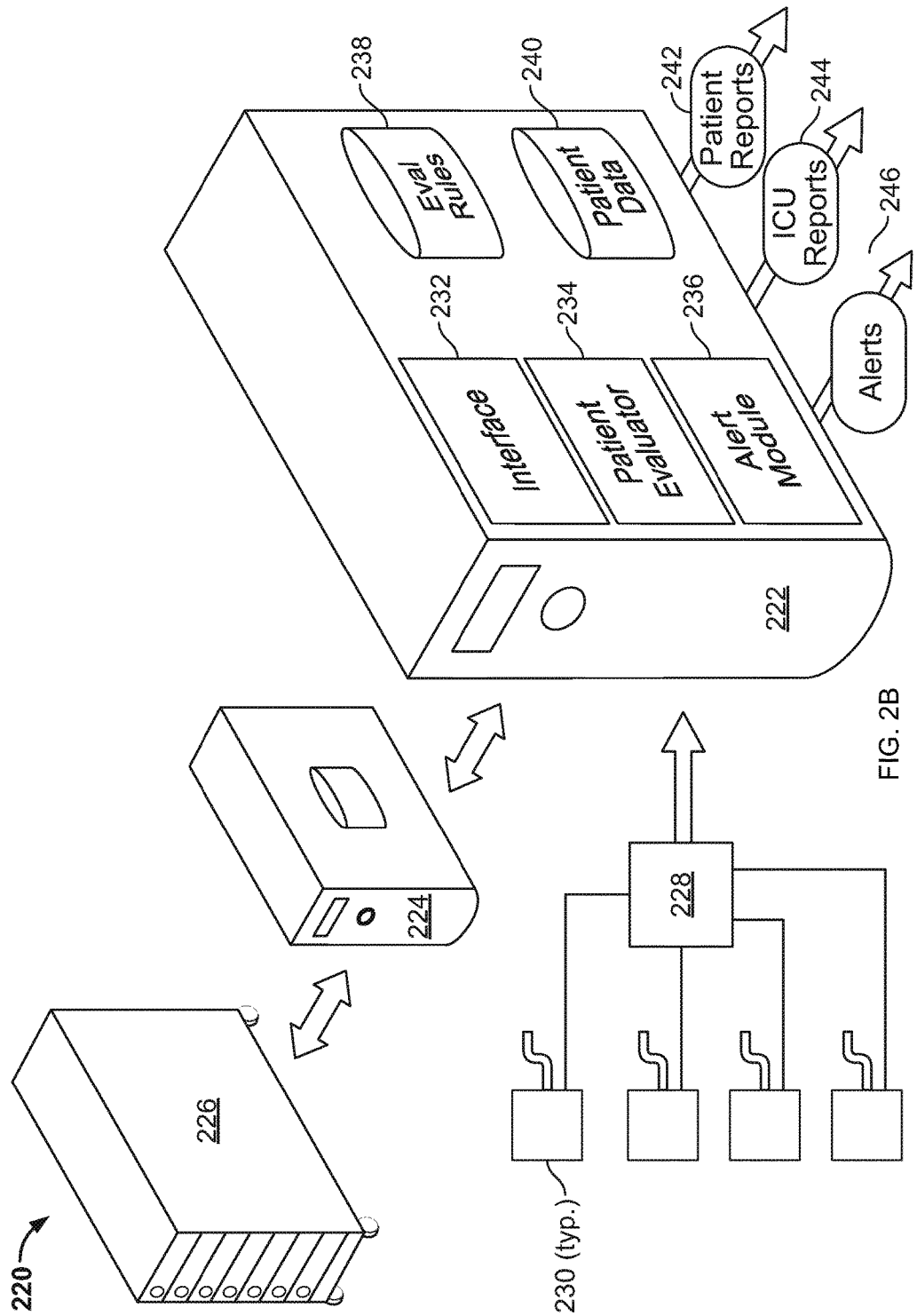
FIG. 2B is a schematic diagram of a computer system for alerting caregivers about ventilation problems with patients in a healthcare facility.

FIG. 2B is a schematic diagram of a computer system 220 for alerting caregivers about ventilation problems with patients in a healthcare facility. In general, the computer system 220 may comprise all or a portion of system 200 (FIG. 2A) in certain implementations though more detail is shown in this figure for certain portions of computer system 220.

The computer system 220 generally includes an alerting computer system 222 which may be made up of one or more computer servers programmed with computer code to analyze various scattered data in a healthcare system so as to generate an alert that a dangerous condition may exist for one or more patients who are using ventilators in the system. The alerting computer system 222 may capture its data from a number of ventilators 230 via a data aggregation unit 228. The unit 228 may include a database that stores and manages various parameters concerning ventilators that are operating in one or more ICU's in a healthcare system, including ventilator setpoints and readings (e.g., respiration rate, oxygen content, etc.) taken by the various ventilators. The unit 228 may also include an interface that operates according to a known application programming interface (API) so that data about the ventilators can be communicated to the alerting computer system 222 in a predefined manner.

The alerting computer system 222 may also gather data from a data warehouse 224, which may take a variety of forms, and is generally designed to be a centralized location where data about a healthcare system may be easily accessed and manipulated. The warehouse 224 may in turn query a data system 226 for the entire healthcare system. The data system 226 is shown here as a rack of servers to indicate that the data system 226 will typically involve a number of different servers scattered across a campus or larger network of healthcare facilities, though the particular physical form of any of the computer systems or sub-systems shown here is not critical and can take any appropriate form.

The alerting computer system 222 includes a variety of components that allow it to obtain data relating to ventilator patients and to generate alerts in appropriate circumstances. An interface 232 is provided so that alerting computer system 222 can query unit 228, data warehouse 224, and other appropriate data stores to obtain information that can be used to determine the condition of a patient or patients. Such data may be used by a patient evaluator, in combination with patient evaluation rules 238 that are stored by the alerting computer system 222, to determine whether a patient could be in a potentially dangerous condition. Patient data 240 may also be stored and used by the patient evaluator 234, such as identification information for the patient, the ICU in which they are staying, etc. Example rules are discussed above and below in more detail.

An alert module 236 may be notified by the patient evaluator 234 when a potentially dangerous condition is determined to exist. The alert module 236 may then gather information about the patient and the alerting condition, and may prepare a message (box 246) to be sent to an appropriate caregiver. The alerting computer system 222 may also generate information in addition to individual alerts. For example, patient reports (box 242) may be generated for administrators who query the alerting computer system 222, and such reports may indicate the number of times an alert has been generated for a particular patient and the nature of the alerts. Such a query may be made by an administrator trying to determine whether alerts have been acted on appropriately, or by a caregiver from the patient's room, to determine how long an alerting condition has existing, in determining a proper remedial plan of care for the patient. Also, more general ICU reports (box 244) may be generated, and may show an administrator a compilation of alert activity for one or more ICU's, which may assist the administrator in staffing caregivers or determining whether appropriate ICU care is being provided.

Figure 3A:
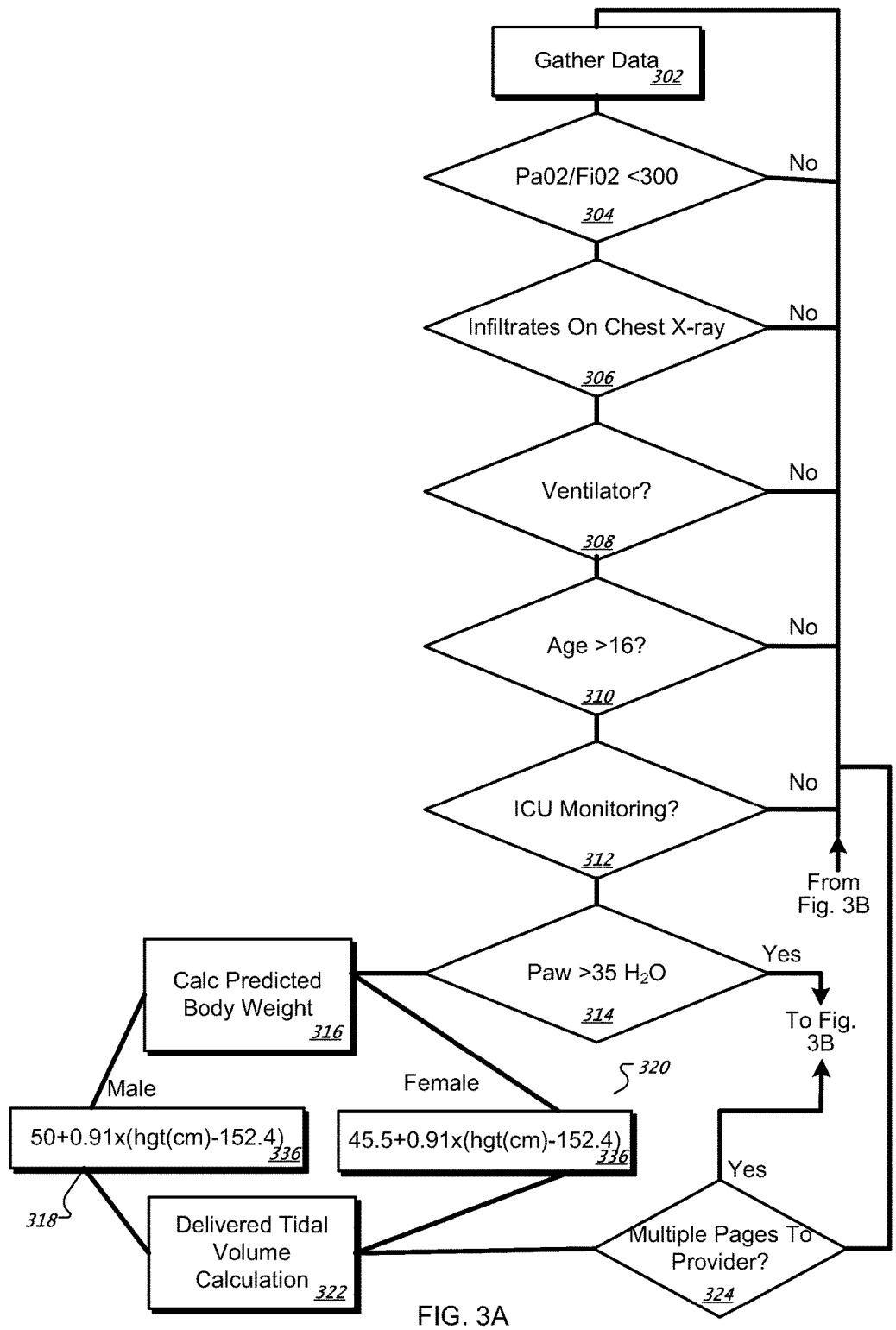
FIGS. 3A and 3B are a flow chart of a process for determining whether to alert a caregiver about a ventilated patient.
Figure 3B:
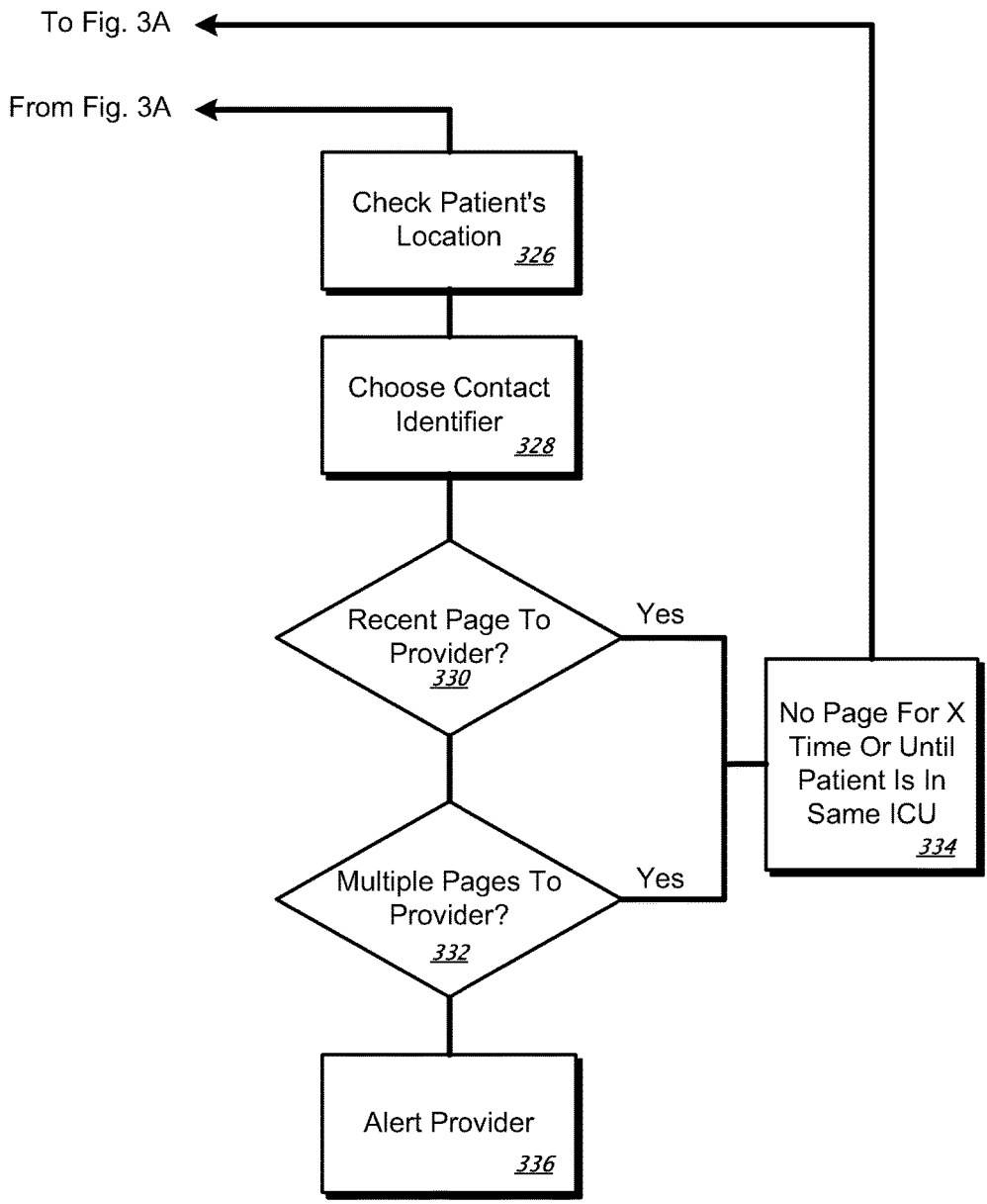

FIGS. 3A and 3B are a flow chart of a process for determining whether to alert a caregiver about a ventilated patient. The process begins at box 302 where data concerning one or more patients currently on ventilators is gathered. Such readings may occur periodically, such as every 5 minutes, every 15 minutes, every half hour, or every hour. Certain of the readings may be updated more often than are other readings that are expected to change less over time. For example, real-time readings from a ventilator may be made frequently, whereas queries made of medical records such as lab results may be made less frequently.

At box 304, the arterial blood gas level for a patient is determined from an EMR reading. If the PaO2/FiO2 level is below 300, no alert is generated, and the process stops for that patient until the next round of data gathering. Likewise, if no textual terms on a chest x-ray report indicate the presence of infiltrates, the process ends for the patient in the current cycle. Similarly, at box 308, if the patient is not on a ventilator, the process stops for the cycle, and if the patient is younger than 16, the process also stops. Similarly, the process stops if the patient is not on ICU monitoring (box 312). Each of these determinations may be conducted in different appropriate orders, and would ordinarily be conducted so that a minimal number of determinations are needed.

The process then makes particular individualized determinations about the patient's current ventilator treatment. First, if the patient's Paw is over 35 mm $H_2O$, a provisional determination to generate an alert is made, and the process moves to FIG. 3B. The provisional determination to trigger an alarm may also depend on a determination that the triggering conditions has existed for more than a certain number of measuring cycles, such as 4 sequential cycles over an hour on a 15 minute repeating schedule. By requiring multiple consistent readings in a row, the process can avoid generating false positive results. Such limits may also be applied for a certain period, such as over the first three days of mechanical ventilation for a patient. In addition, weaning modes of mechanical ventilations such as pressure support, may also be eliminated to minimize the impact of artificial values (e.g., high airway pressure due to cough or patient manipulation).

If the Paw is not over 35, then the patient's predicted body weight (PBW) is calculated according to the equations shown in boxes 318 (if the patient is male) or 320 (if the patient is female). The delivered tidal volume for the patient is then determined at box 322, and a determination is made at box 324 of whether the tidal volume is greater than 8 ml/kq of PBW. If the volume does not exceed that amount, the process ends for the current cycle for the patient. If the volume does exceed that amount, then a provisional determination to generate an alert is made and the process moves to FIG. 3B.

In FIG. 3B, determinations are made with respect to whether a provisional determination to generate an alert should result in an actual alert being generated. In particular, it may not be helpful to patients to generate an alert every time the numbers above indicate that a potentially dangerous (e.g., potentially injurious) condition exists, because over alerting is known not to result in improved care. Thus, at box 326, the patient's location is checked, and a contact identifier for a caregiver is determined at box 328. The contact identifier may be a pager or e-mail or text message in EMR address for whatever caregiver is currently on call for the ICU where the patient is staying. Two determinations are then made that may result in the notification (e.g., in the form of a text page), a determination is made whether a recent page has been given to the caregiver or provide (box 330). If a recent alert was given, and the ventilator settings were not changed, it may indicate that the provider responded to the alert but decided to leave the ventilator in its existing state. Such a provider may not wish to be alerted again in a short time period. If so, the alert is held for a predetermined time period or until the patient is located in the same ICU as the caregiver (box 334) (so as to minimize the time that the caregiver will have to take away from other important work in order to answer the alert).

Second, a determination is made whether multiple pages above a certain number have been made to the caregiver about the patient in a certain prior time period leading up to the current time (box 332). Again, if so, the page or other form of notification may be held up or delayed. If neither limiting condition exists, the alert may be provided to the relevant caregiver (box 334), and data stores that track the number of alerts that have been given can be incremented with time-stamped entries so that the determinations of boxes 330 and 332 may be accurately made in futures rounds of the process.

Example 1

A ten-month study was conducted on 5118 patient admissions at an intensive care unit in a large healthcare system. Subjects were included if they were on a ventilator. Patients were excluded if they were under 16 years old, did not provide research authorization, were ventilated less than 12 hours or less than 49 PEEP measurements, were readmitted to the hospital during the study period, or were already being ventilated when the study began. The prevalence of ALI was 10% among 2944 patients receiving invasive ventilation during the study period. The system sent 69 alerts for 56 patients. Of the alerts, 14 were false positives (25%), seven resulted in decreased tidal volume (12%), five resulted in a changed mode of ventilation (9%), six resulted in increased sedation or neuromuscular blockage (11%), and twenty-four resulted in no intervention (43%).

Analysis indicated that 6.1% of patients has median pleural pressure, Ppl>30 before the intervention and 5.65% had it after. The analysis also showed that 3.57% of the patients had median tidal volume, Vt>8 mL·kg PBW before intervention, and 8.04% had it after.

Example 2

A study of a cohort of 485 consecutively admitted critically ill patients in a medical ICU of a tertiary center was conducted (less 38 patients who denied research authorization). A system for reviewing a near-real time copy of the patient medical record was used in combination with readings from a ventilator to generate an electronic alert. Reports from emergency portable chest radiographs were consulted for data concerning patient lung condition.

ALI was defined according to standard consensus conference criteria. See Bernard GR., et al., Am J. Respiratory Critical Care Medicine 149, pages 818-24 (1994) An electronic alert was triggered by a combination of observations within a 24 hour period: (1) qualifying arterial blood gas analysis: the ratio of partial pressure of oxygen over inspired oxygen concentration (PaO2/FiO2)<300, and (2) qualifying chest radiograph report: free text Boolean query containing trigger words: ("bilateral" AND "infiltrate") OR "edema."

From the 485 consecutive patients, 54 patients were identified with ALI (11%). Sensitivity and specificity of the alert was determined against a gold standard of prospective assessment by a trained study coordinator who was blinded to the alert. The alert generated good sensitivity, 93% (95% CI 90 to 95) and specificity, 90% (95% CI 87 to 92), with a positive predictive value of 53% (95% CI 49 to 58) and a negative predictive value of 99% (95% CI 98 to 100). Likelihood ratio for positive result was 9.07 and for negative −0.08. The main reasons for false positives were cardiogenic pulmonary edema and atelectasis. The alert identified patients with ALI within twenty-four hours from the onset in all cases.

Figure 4:
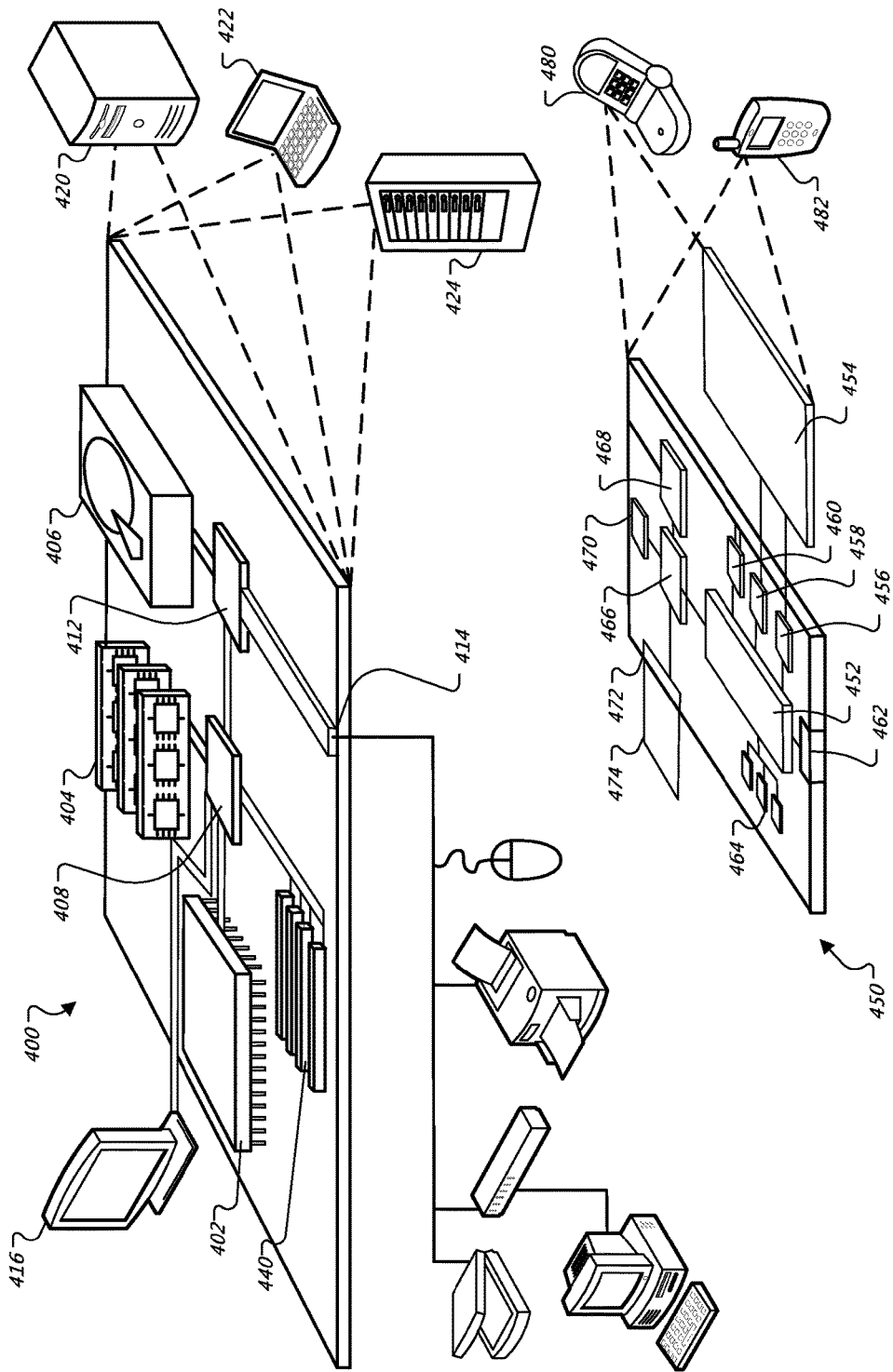
FIG. 4 shows an example of a generic computer device and a generic mobile computer device, which may be used with the techniques described here.

FIG. 4 shows an example of a generic computer device 400 and a generic mobile computer device 450, which may be used with the techniques described here. Computing device 400 is intended to represent various forms of digital computers, such as laptops, desktops, workstations, personal digital assistants, servers, blade servers, mainframes, and other appropriate computers. Computing device 450 is intended to represent various forms of mobile devices, such as personal digital assistants, cellular telephones, smartphones, and other similar computing devices. The components shown here, their connections and relationships, and their functions, are meant to be exemplary only, and are not meant to limit implementations of the inventions described and/or claimed in this document.

Computing device 400 includes a processor 402, memory 404, a storage device 406, a high-speed interface 408 connecting to memory 404 and high-speed expansion ports 440, and a low speed interface 412 connecting to low speed bus 414 and storage device 406. Each of the components 402, 404, 406, 408, 440, and 412, are interconnected using various busses, and may be mounted on a common motherboard or in other manners as appropriate. The processor 402 can process instructions for execution within the computing device 400, including instructions stored in the memory 404 or on the storage device 406 to display graphical information for a GUI on an external input/output device, such as display 416 coupled to high speed interface 408. In other implementations, multiple processors and/or multiple buses may be used, as appropriate, along with multiple memories and types of memory. Also, multiple computing devices 400 may be connected, with each device providing portions of the necessary operations (e.g., as a server bank, a group of blade servers, or a multi-processor system).

The memory 404 stores information within the computing device 400. In one implementation, the memory 404 is a volatile memory unit or units. In another implementation, the memory 404 is a non-volatile memory unit or units. The memory 404 may also be another form of computer-readable medium, such as a magnetic or optical disk.

The storage device 406 is capable of providing mass storage for the computing device 400. In one implementation, the storage device 406 may be or contain a computer-readable medium, such as a floppy disk device, a hard disk device, an optical disk device, or a tape device, a flash memory or other similar solid state memory device, or an array of devices, including devices in a storage area network or other configurations. A computer program product can be tangibly embodied in an information carrier. The computer program product may also contain instructions that, when executed, perform one or more methods, such as those described above. The information carrier is a computer- or machine-readable medium, such as the memory 404, the storage device 406, memory on processor 402, or a propagated signal.

The high speed controller 408 manages bandwidth-intensive operations for the computing device 400, while the low speed controller 412 manages lower bandwidth-intensive operations. Such allocation of functions is exemplary only. In one implementation, the high-speed controller 408 is coupled to memory 404, display 416 (e.g., through a graphics processor or accelerator), and to high-speed expansion ports 440, which may accept various expansion cards (not shown). In the implementation, low-speed controller 412 is coupled to storage device 406 and low-speed expansion port 414. The low-speed expansion port, which may include various communication ports (e.g., USB, Bluetooth, Ethernet, wireless Ethernet) may be coupled to one or more input/output devices, such as a keyboard, a pointing device, a scanner, or a networking device such as a switch or router, e.g., through a network adapter.

The computing device 400 may be implemented in a number of different forms, as shown in the figure. For example, it may be implemented as a standard server 420, or multiple times in a group of such servers. It may also be implemented as part of a rack server system 424. In addition, it may be implemented in a personal computer such as a laptop computer 422. Alternatively, components from computing device 400 may be combined with other components in a mobile device (not shown), such as device 450. Each of such devices may contain one or more of computing device 400, 450, and an entire system may be made up of multiple computing devices 400, 450 communicating with each other.

Computing device 450 includes a processor 452, memory 464, an input/output device such as a display 454, a communication interface 466, and a transceiver 468, among other components. The device 450 may also be provided with a storage device, such as a microdrive or other device, to provide additional storage. Each of the components 450, 452, 464, 454, 466, and 468, are interconnected using various buses, and several of the components may be mounted on a common motherboard or in other manners as appropriate.

The processor 452 can execute instructions within the computing device 450, including instructions stored in the memory 464. The processor may be implemented as a chipset of chips that include separate and multiple analog and digital processors. The processor may provide, for example, for coordination of the other components of the device 450, such as control of user interfaces, applications run by device 450, and wireless communication by device 450.

Processor 452 may communicate with a user through control interface 458 and display interface 456 coupled to a display 454. The display 454 may be, for example, a TFT LCD (Thin-Film-Transistor Liquid Crystal Display) or an OLED (Organic Light Emitting Diode) display, or other appropriate display technology. The display interface 456 may comprise appropriate circuitry for driving the display 454 to present graphical and other information to a user. The control interface 458 may receive commands from a user and convert them for submission to the processor 452. In addition, an external interface 462 may be provide in communication with processor 452, so as to enable near area communication of device 450 with other devices. External interface 462 may provide, for example, for wired communication in some implementations, or for wireless communication in other implementations, and multiple interfaces may also be used.

The memory 464 stores information within the computing device 450. The memory 464 can be implemented as one or more of a computer-readable medium or media, a volatile memory unit or units, or a non-volatile memory unit or units. Expansion memory 474 may also be provided and connected to device 450 through expansion interface 472, which may include, for example, a SIMM (Single In Line Memory Module) card interface. Such expansion memory 474 may provide extra storage space for device 450, or may also store applications or other information for device 450. Specifically, expansion memory 474 may include instructions to carry out or supplement the processes described above, and may include secure information also. Thus, for example, expansion memory 474 may be provide as a security module for device 450, and may be programmed with instructions that permit secure use of device 450. In addition, secure applications may be provided via the SIMM cards, along with additional information, such as placing identifying information on the SIMM card in a non-hackable manner.

The memory may include, for example, flash memory and/or NVRAM memory, as discussed below. In one implementation, a computer program product is tangibly embodied in an information carrier. The computer program product contains instructions that, when executed, perform one or more methods, such as those described above. The information carrier is a computer- or machine-readable medium, such as the memory 464, expansion memory 474, memory on processor 452, or a propagated signal that may be received, for example, over transceiver 468 or external interface 462.

Device 450 may communicate wirelessly through communication interface 466, which may include digital signal processing circuitry where necessary. Communication interface 466 may provide for communications under various modes or protocols, such as GSM voice calls, SMS, EMS, or MMS messaging, CDMA, TDMA, PDC, WCDMA, CDMA2000, or GPRS, among others. Such communication may occur, for example, through radio-frequency transceiver 468. In addition, short-range communication may occur, such as using a Bluetooth, WiFi, or other such transceiver (not shown). In addition, GPS (Global Positioning System) receiver module 470 may provide additional navigation- and location-related wireless data to device 450, which may be used as appropriate by applications running on device 450.

Device 450 may also communicate audibly using audio codec 460, which may receive spoken information from a user and convert it to usable digital information. Audio codec 460 may likewise generate audible sound for a user, such as through a speaker, e.g., in a handset of device 450. Such sound may include sound from voice telephone calls, may include recorded sound (e.g., voice messages, music files, etc.) and may also include sound generated by applications operating on device 450.

The computing device 450 may be implemented in a number of different forms, as shown in the figure. For example, it may be implemented as a cellular telephone 480. It may also be implemented as part of a smartphone 482, personal digital assistant, or other similar mobile device.

Various implementations of the systems and techniques described here can be realized in digital electronic circuitry, integrated circuitry, specially designed ASICs (application specific integrated circuits), computer hardware, firmware, software, and/or combinations thereof. These various implementations can include implementation in one or more computer programs that are executable and/or interpretable on a programmable system including at least one programmable processor, which may be special or general purpose, coupled to receive data and instructions from, and to transmit data and instructions to, a storage system, at least one input device, and at least one output device.

These computer programs (also known as programs, software, software applications or code) include machine instructions for a programmable processor, and can be implemented in a high-level procedural and/or object-oriented programming language, and/or in assembly/machine language. As used herein, the terms "machine-readable medium" "computer-readable medium" refers to any computer program product, apparatus and/or device (e.g., magnetic discs, optical disks, memory, Programmable Logic Devices (PLDs)) used to provide machine instructions and/or data to a programmable processor, including a machine-readable medium that receives machine instructions as a machine-readable signal. The term "machine-readable signal" refers to any signal used to provide machine instructions and/or data to a programmable processor.

To provide for interaction with a user, the systems and techniques described here can be implemented on a computer having a display device (e.g., a CRT (cathode ray tube) or LCD (liquid crystal display) monitor) for displaying information to the user and a keyboard and a pointing device (e.g., a mouse or a trackball) by which the user can provide input to the computer. Other kinds of devices can be used to provide for interaction with a user as well; for example, feedback provided to the user can be any form of sensory feedback (e.g., visual feedback, auditory feedback, or tactile feedback); and input from the user can be received in any form, including acoustic, speech, or tactile input.

The systems and techniques described here can be implemented in a computing system that includes a back end component (e.g., as a data server), or that includes a middleware component (e.g., an application server), or that includes a front end component (e.g., a client computer having a graphical user interface or a Web browser through which a user can interact with an implementation of the systems and techniques described here), or any combination of such back end, middleware, or front end components. The components of the system can be interconnected by any form or medium of digital data communication (e.g., a communication network). Examples of communication networks include a local area network ("LAN"), a wide area network ("WAN"), and the Internet.

The computing system can include clients and servers. A client and server are generally remote from each other and typically interact through a communication network. The relationship of client and server arises by virtue of computer programs running on the respective computers and having a client-server relationship to each other.

A number of embodiments have been described. Nevertheless, it will be understood that various modifications may be made without departing from the spirit and scope of the invention. For example, much of this document has been described with respect to ICU monitoring with attending physicians, but other forms of patient monitoring and reporting may also be addressed.

In addition, the logic flows depicted in the figures do not require the particular order shown, or sequential order, to achieve desirable results. In addition, other steps may be provided, or steps may be eliminated, from the described flows, and other components may be added to, or removed from, the described systems. Accordingly, other embodiments are within the scope of the following claims.

What is claimed is:

1. A computer-implemented patient information provisioning method, comprising:
   identifying, as key words, terms likely to occur in electronic medical records that are determined to indicate presence of acute lung injury or acute respiratory distress syndrome;
   automatically extracting with a computer system and the identified terms, from records maintained for a patient under care in a healthcare facility, information from an electronic medical record, and automatically analyzing text of the electronic medical record to determine whether the patient under care has acute lung injury or acute respiratory distress syndrome, wherein the automatically extracting comprises querying written textual descriptions in patient reports for the identified key words that are indicative of acute lung injury or acute respiratory distress syndrome;
   obtaining with the computer system, and as a result of identifying in the analyzed text of the electronic medical record key words that are determined to indicate presence of acute lung injury or acute respiratory distress syndrome, information about a medical ventilator currently treating the patient;
   adjusting an operational value for the medical ventilator from a normal value that is used for patients who do not have acute lung injury or acute respiratory distress syndrome, based on determining that an improper setting exists for the patient as a combination of (a) the patient's electronic medical record having one or more key words that are indicative of acute lung injury or acute respiratory distress syndrome, and (b) the medical ventilator having a current value inconsistent with treatment of someone with acute lung injury or acute respiratory distress syndrome;
   determining that a potentially dangerous condition exists for the patient based on a measured value for the medical ventilator being excessive compared to the adjusted operational value;
   identifying a contact identifier for a device of a caregiver based on a determination of who is currently assigned responsibility for the patient, and as a result of determining that the potentially dangerous condition exists; and
   electronically alerting the caregiver remote from the patient if it is determined that the potentially dangerous condition exists.

2. The method of claim 1, wherein the information from the electronic medical record comprises data from an arterial blood gas analysis.

3. The method of claim 1, further comprising obtaining with the computer system textual information from a medical report for the patient and using the textual information to determine whether a potentially dangerous condition exists with respect to the medical ventilator.

4. The method of claim 1, wherein the information about the medical ventilator comprises information about a measured peak pressure or set tidal volume for the medical ventilator.

5. The method of claim 4, wherein the potentially dangerous condition is determined to exist if the information from the electronic medical record indicates an arterial blood gas level of $PaO_2/FIO_2 < 300$ mmHg, pressure is above 35 mm $H_2O$ or volume is above 8 mL/kg.

6. The method of claim 1, wherein electronically alerting a caregiver comprises providing an electronic messaging service with a description of an alerting condition of the patient, and information identifying the patient.

7. The method of claim 1, further comprising blocking alerting of the caregiver if the caregiver has previously been notified about the patient a predetermined number of times in a predetermined time period.

8. The computer-implemented method of claim 1, further comprising receiving an input from the caregiver to control the medical ventilator.

9. The computer-implemented method of claim 1, wherein the information from the electronic medical record does not indicate a diagnosis of acute lung injury or acute respiratory distress syndrome.

10. The computer-implemented method of claim 1, further comprising suppressing the electronic alerting of the caregiver until the potentially dangerous condition has been determined to have persisted for a particular time period.

11. The computer-implemented method of claim 1, further comprising suppressing the electronic alerting of the caregiver upon determining that prior alerts have been provided to the caregiver.

12. The computer-implemented method of claim 1, wherein a determination about whether a potentially dangerous condition exists is based on a first group of data that is obtained repeatedly at a first frequency, and a second group of data that is obtained at a different, second frequency, wherein the frequencies depend on how frequently the groups of data are expected to change over time.

13. The computer-implemented method of claim 1, wherein a determination about whether a potentially dangerous condition exists comprises making a provisional determination based on a first set of data, and if the provisional determination is positive regarding a potentially dangerous condition existing, making a final determination using a second set of data.

14. The computer-implemented method of claim 1, wherein determining that a potentially dangerous condition exists for the patient further comprises natural language processing of text in the electronic medical record.

15. The computer-implemented method of claim 1, further comprising automatically changing settings of the medical ventilator as a result of determining that a potentially dangerous condition exists for the patient.

16. The computer-implemented method of claim 1, further comprising delaying the electronic alerting of the caregiver based on a determination of prior alerts that have been provided for the patient.

17. The computer-implemented method of claim 1, further comprising determining a particular location of the patient to identify the contact identifier of the caregiver.

18. A computing system, comprising:
a medical ventilator for providing mechanical ventilation to a patient;
one or more processors;
memory; and
one or more programs, wherein the one or more programs are stored in the memory and configured to be executed by the one or more processors, the one or more programs including:
instructions for identifying, as key words, terms likely to occur in electronic medical records that are determined to indicate presence of acute lung injury or acute respiratory distress syndrome;
instructions for automatically extracting, from records maintained for the patient, information from an electronic medical record, and automatically analyzing text of the electronic medical record to determine whether the patient under care has acute lung injury or acute respiratory distress syndrome, wherein the automatically extracting comprises querying written textual descriptions in patient reports for the identified key words that are indicative of acute lung injury or acute respiratory distress syndrome;
instructions for obtaining with the computing system, and as a result of identifying in the analyzed text of the electronic medical record key words that are determined to indicate presence of acute lung injury or acute respiratory distress syndrome, current information about the medical ventilator;
instructions for adjusting an operational value for the medical ventilator from a normal value that is used for patients who do not have acute lung injury or acute respiratory distress syndrome, based on determining that an improper setting exists for the patient as a combination of (a) the patient's electronic medical record having one or more key words that are indicative of acute lung injury or acute respiratory distress syndrome, and (b) the medical ventilator having a current value inconsistent with treatment of someone with acute lung injury or acute respiratory distress syndrome;
instructions for determining that a potentially dangerous condition exists for the patient based on a measured value for the medical ventilator being excessive compared to the adjusted operational value;
instructions for identifying a contact identifier for a device of a caregiver based on a determination of who is currently assigned responsibility for a location of the patient in the medical facility; and
instructions for electronically alerting the caregiver remote from the patient if it is determined that the potentially dangerous condition exists.

19. The system of claim 18, wherein the information from the electronic medical record comprises data from an arterial blood gas analysis.

20. The system of claim 18, further comprising instructions for obtaining textual information from a medical report for the patient and using the textual information to determine whether the potentially dangerous condition exists with respect to the medical ventilator.

21. The system of claim 18, wherein the information about the medical ventilator comprises information about a measured peak pressure or set tidal volume for the medical ventilator.

22. The system of claim 21, wherein a potential dangerous condition is determined to exist if the information from the electronic medical record indicates an arterial blood gas level of $PaO_2/FIO_2<300$ mmHg, and pressure is above 35 mm $H_2O$ or volume is above 8 mL/kg predicted body weight.

23. The system of claim 18, wherein electronically alerting a caregiver comprises providing an electronic messaging service with a description of an alerting condition of the patient, and information identifying the patient.

24. The system of claim 18, further comprising instructions for blocking alerting of the caregiver if the caregiver has previously been notified about the patient a predetermined number of times in a predetermined time period.

25. A computer-implemented patient information provisioning system, comprising:
one or more mechanical ventilators for treating patients in a healthcare facility;
an interface operating on a computer processor system programmed to identify, as key words, terms likely to occur in electronic medical records that are determined to indicate presence of acute lung injury or acute respiratory distress syndrome, and obtain (a) data about operating parameters of the one or more mechanical ventilators, including information about the location(s) of the one or more mechanical ventilators, (b) information for electronically contacting particular caregivers who correspond to patients served by the one or more mechanical ventilators and are identified for contact based on a determination of what caregiver is currently assigned responsibility for a location in the healthcare facility that currently needs action by a caregiver, and (c) data from a central electronic medical records system operated by the healthcare facility, wherein the patient information provisioning system is programmed to automatically query written textual descriptions by caregivers in electronic medical records of the electronic medical record system to determine whether trigger terms in the records indicate that one or more particular patients under care have acute lung injury or acute respiratory distress syndrome;
an electronic patient evaluator to use the data about the current operating parameters of the one or more mechanical ventilators and the data from the central electronic medical records system to
(1) adjust an operational value for a first mechanical ventilator, of the one or more mechanical ventilators, from a normal value that is used for patients who do not have acute lung injury or respiratory distress syndrome, based on determining that a dangerous condition exists for a first patient as a combination of
  (a) the first patient's electronic medical record having one or more key words that are indicative of acute lung injury or acute respiratory distress syndrome, and
  (b) the first mechanical ventilator having a current value inconsistent with treatment of someone with acute lung injury or acute respiratory distress syndrome;
(2) determine that a potentially dangerous condition exists for the first patient based on a measured value for the first mechanical ventilator being excessive compared to the adjusted operational value; and
(3) identify that the first patient is receiving an inappropriate low tidal volume from the first mechanical ventilator by determining that a measured value for the first mechanical ventilator is excessive compared to the adjusted operational value; and
an alert module to provide, for transmission to one or more caregivers who are remote from the first mechanical ventilator, a notification of the identified dangerous condition.

* * * * *